US008481751B2

(12) United States Patent
Groh et al.

(10) Patent No.: US 8,481,751 B2
(45) Date of Patent: Jul. 9, 2013

(54) PROCESS FOR THE PRODUCTION OF BENDAMUSTINE ALKYL ESTER, BENDAMUSTINE, AND DERIVATIVES THEREOF

(75) Inventors: Kai Groh, Rüsselsheim (DE); Holger Rauter, Flieden (DE); Dirk Born, Biebergemünd (DE)

(73) Assignee: Heraeus Precious Metals GmbH & Co. KG, Hanau (DE)

( * ) Notice: Subject to any disclaimer, the term of this patent is extended or adjusted under 35 U.S.C. 154(b) by 1 day.

(21) Appl. No.: 13/334,402

(22) Filed: Dec. 22, 2011

(65) Prior Publication Data
US 2012/0165543 A1 Jun. 28, 2012

Related U.S. Application Data

(60) Provisional application No. 61/426,098, filed on Dec. 22, 2010.

(30) Foreign Application Priority Data

Dec. 22, 2010 (DE) .......................... 10 2010 055 499

(51) Int. Cl.
*C07D 235/12* (2006.01)
(52) U.S. Cl.
USPC ....................................................... 548/310.1
(58) Field of Classification Search
USPC ....................................................... 548/310.1
See application file for complete search history.

(56) References Cited

U.S. PATENT DOCUMENTS
6,245,954 B1 6/2001 Weyer et al.

FOREIGN PATENT DOCUMENTS
| DE | 34727 A1 | 12/1964 |
| DE | 159877 A1 | 4/1983 |
| DE | 19824929 A1 | 12/1999 |

OTHER PUBLICATIONS

Search Report and Written Opinion issued Oct. 5, 2012 in SG Application No. 201109252-5.
Office Action issued Nov. 16, 2012 in AU Application No. 2011265491.
Ozegowski et al, "Omega-[Bis-(Beta-chlorathyl)-amino-benzimidazolyl-(2)]-propion-bzw.-buttersäuren als potentielle Cytostatika," Journal für praktische Chemie., vol. 20, No. 4, pp. 178-186 (1963).
Search Report issued Apr. 16, 2012 in EP Application No. 11009886.0.
Werner et al, "Synthesis of a potential metabolite of the anticancer drug bendamustine (CytostasanR)", Die Pharmazie, vol. 46, No. 2, pp. 113-114 (1991).
Werner et al, "Hydrolyseprodukte des Cencerostaticums Cytostasan (Bendamustin)", Die Pharmazie, vol. 42, No. 4, pp. 272-273 (1987).
Gust et al, "Investigations on the stability of bendamustin, a cytostatic agent of the nitrogen mustard type, I. Synthesis, Isolation, and characterization of reference substances", Chemical Monthly, vol. 128, pp. 291-299 (1997).
Adams et al., "Action of Oxalyl Chloride on Primary, Secondary and Teritiary Alcohols", Journal American Chemical Society, vol. 38, pp. 2514-2519, (1916).
DE Office Action issued Jun. 7, 2011 in German Application No. 10 2010 055 499.5.
English translation of an Office Action issued Mar. 5, 2013 in RU Application No. 2011152372/04.

*Primary Examiner* — Laura L. Stockton
(74) *Attorney, Agent, or Firm* — Panitch Schwarze Belisario & Nadel LLP

(57) ABSTRACT

Methods are provided for the production of bendamustine alkyl ester, bendamustine, as well as derivatives thereof. With the methods the production of these compounds is possible in reproducibly high yields. To this end, hydroxyl-group-containing esters are used as the starting material, whose hydroxyl groups are substituted in a simple way by halogen groups. This substitution is possible in the presence of (i) oxalyl chloride and (ii) dialkylformamide, dialkyl acetamide or dimethyl sulfoxide. In a subsequent reaction, the resulting esters can be hydrolyzed to form the acid.

18 Claims, No Drawings

PROCESS FOR THE PRODUCTION OF BENDAMUSTINE ALKYL ESTER, BENDAMUSTINE, AND DERIVATIVES THEREOF

CROSS-REFERENCE TO RELATED APPLICATION

Applicant hereby claims the benefit of U.S. provisional application No. 61/426,098, filed Dec. 22, 2010, the disclosure of which is incorporated herein by reference.

BACKGROUND OF THE INVENTION

The present invention relates to a method for the production of ester compounds that are represented by the formula (I)

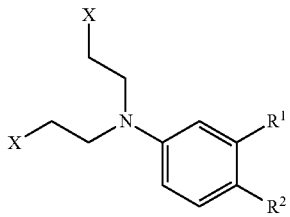

or salts thereof, where X stands for a halogen radical, $R^1$ and $R^2$ are selected so that (1) $R^1$ is H and $R^2$ is $-CH_2(CH_2)_m COOR^3$, (2) $R^1$ is $-CH_2(CH_2)_m COOR^3$ and $R^2$ is H or (3) $R^1$ and $R^2$ together stand for a radical represented by the formula (II)

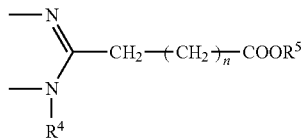

where each of $R^3$, $R^4$ and $R^5$ stands independently for an alkyl radical, and where each of m and n represents independently a number in the range of 0-12. The present invention likewise relates to a method for the production of the correspondingly hydrolyzed ester, i.e., a compound represented by the formula (VII)

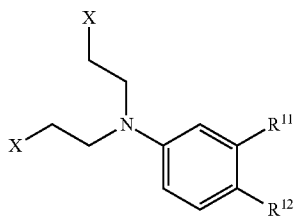

or a salt thereof, where X stands for a halogen radical, $R^{11}$ and $R^{12}$ are selected so that (1) $R^{11}$ is H and $R^{12}$ is $-CH_2(CH_2)_m COOH$, (2) $R^{11}$ is $CH_2(CH_2)_m COOH$ and $R^{12}$ is H or (3) $R^{11}$ and $R^{12}$ together stand for a radical represented by the formula (VIII)

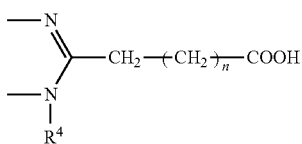

where $R^4$ stands for an alkyl radical and where each of m and n represents independently a number in the range of 0-12.

Compounds having the structure according to formula (VII) named above are used for chemotherapy for various cancers. Their effect involves the alkylation of endogenous DNA or RNA, which leads, in particular, to a prevention of DNA replication and consequently to apoptosis of the corresponding cells. The fields of use of the mentioned compounds comprise primarily the treatment of various leukemias and lymphomas, multiple myeloma, and bronchial carcinoma. Structurally, these compounds are derived from nitrogen mustard.

Bendamustine 4-[5-[bis(2-chloroethyl)amino]-1-methyl-benzimidazole-2-yl]butanoic acid, which is a representative of this group, was first described in 1963 by Ozegowski and Krebs (*J. Pract. Chem.*, 20: 178-86 (1963)).

One advantageous method for the production of bendamustine is known from German Democratic Republic Patent DD 34727. The synthesis disclosed therein is carried out via the corresponding bendamustine ester, 4-[5-[bis(2-chloroethyl)amino]-1-methylbenzimidazole-2-yl]butanoic acid ester, which is produced by the chlorination of 4-[5-[bis(2-hydroxyethyl)amino]-1-methylbenzimidazole-2-yl]butanoic acid ester. Thionyl chloride is used for the substitution of the two terminal hydroxyl groups of this starting compound by chlorine. Bendamustine can actually be obtained in significant quantities with the method described in DD 34727. A disadvantage in this method, however, is that bendamustine is delivered in very unsteady yields that also fall significantly even if the starting materials are increased.

To solve this problem, it is proposed in German Democratic Republic Patent DD 159877 to stir the reaction mixture of thionyl chloride and 4-[5-[bis(2-hydroxyethyl)amino]-1-methylbenzimidazole-2-yl]butanoic acid ester for the termination of the reaction directly in aqueous hydrochloric acid, whereby the excess thionyl chloride is broken down. Through this measure, a quantitative increase in the yields of bendamustine ester and finally also bendamustine can be achieved.

In further tests, however, it has been shown that even with the method of DD 159877, an increase of the yield of bendamustine ester or bendamustine to greater than 80% is not to be achieved. In addition, it was determined that, in the case of this method, byproducts are produced that can be separated from bendamustine ester or bendamustine only with difficulty and thus negatively influence the product quality. The resulting yields of bendamustine ester or bendamustine also cannot be obtained in a reproducible way, but instead fluctuated considerably despite maintaining the same test conditions. This was shown, in particular, in the test to carry out the method of DD 159877 on an industrial scale. Here, the control of the reaction proved to be difficult due to the high required excess of thionyl chloride. Another problem is produced from the viewpoint of processing economics due to the fact that, when thionyl chloride is used, large quantities of acidic process exhaust gases are generated, placing high demands on the exhaust-gas purification. Similar problems result when the method of DD 159877 is transferred to the production of other compounds that can be represented by the formulas (I) or (VII).

BRIEF SUMMARY OF THE INVENTION

In consideration of the prior art, the problem forming the basis of the present invention consists in providing a method that allows the production of compounds with the structures shown above in reproducibly high yields. Furthermore, the method should also be able to be carried out easily on an industrial scale. In addition, for this method, large quantities of acidic process exhaust gases should not be generated.

This problem was solved by the methods of the present invention, which provides a method for the production of a compound represented by the formula (I)

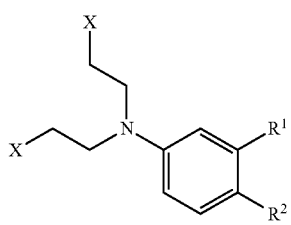

or a salt thereof, where X stands for a halogen radical, $R^1$ and $R^2$ are selected so that (1) $R^1$ is H and $R^2$ is —$CH_2(CH_2)_m COOR^3$, (2) $R^1$ is —$CH_2(CH_2)_m COOR^3$ and $R^2$ is H or (3) $R^1$ and $R^2$ together stand for a radical represented by the formula (II)

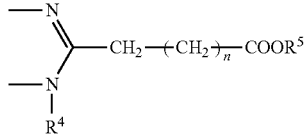

where each of $R^3$, $R^4$ and $R^5$ stands independently for an alkyl radical, and where each of m and n represents independently a number in the range of 0-12, wherein a compound represented by the formula (III)

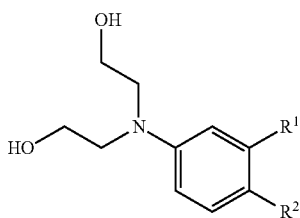

is brought into reaction with a mixture that contains a compound (i) selected from the group consisting of a compound represented by the formula (IV)

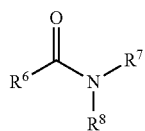

where $R^6$ stands for H or an alkyl radical, and each of $R^7$ and $R^8$ stands independently for an alkyl radical, and of a compound represented by the formula (V)

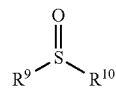

where each of $R^9$ and $R^{10}$ stands independently for an alkyl radical, and this mixture also contains a compound (ii) represented by the formula (VI)

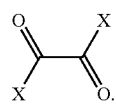

The invention further provides a method for the production of a compound represented by the formula (VII)

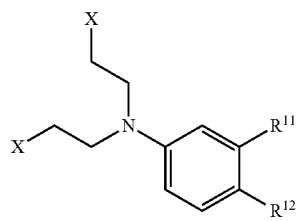

or a salt thereof, where X stands for a halogen radical, $R^{11}$ and $R^{12}$ are selected so that (1) $R^{11}$ is H and $R^{12}$ is —$CH_2(CH_2)_m COOH$, (2) $R^{11}$ is —$CH_2(CH_2)_m COOH$ and $R^{12}$ is H or (3) $R^{11}$ and $R^{12}$ together stand for a radical represented by the formula (VIII)

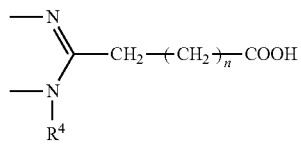

where $R^4$ stands for an alkyl radical and where each of m and n represents independently a number in the range of 0-12, and wherein the method described above is carried out and the resulting ester compound represented by the formula (I) undergoes ester hydrolysis.

Surprisingly, it was determined that through the use of a mixture comprising at least one of the compounds according to formulas (IV) and (V), as well as the compound according to formula (VI), the terminal hydroxyl groups in the compound according to formula (I) can be selectively substituted under mild conditions and at moderate reaction times by halogenide groups, wherein the desired product is obtained in high yields in a reproducible way. Without wanting to be bound to one theory, this reaction definitely proceeds via an intermediately formed, activated iminium ion, formed from the compound according to formula (IV) or (V), as well as the compound according to formula (VI).

DETAILED DESCRIPTION OF THE INVENTION

The method according to the invention comprises, on one hand, the production of a compound represented by the formula (I)

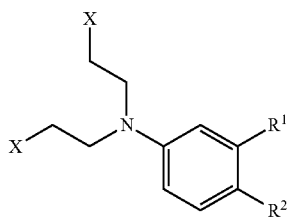

or a salt thereof.

In formula (I), the radical X stands for a halogen radical. The halogen radical can involve, for example, a chlorine radical or a bromine radical. According to the invention, both radicals X in formula (I) stand for the same substituents. According to one especially preferred embodiment, these halogen radicals are chlorine radicals.

The radicals $R^1$ and $R^2$ can assume different meanings.

According to a first alternative (1), the radical $R^1$ comprises hydrogen. In this case, the radical $R^2$ stands for the radical —$CH_2(CH_2)_mCOOR^3$. In this radical, $R^3$ stands for an alkyl radical. The alkyl radical can involve a branched or non-branched alkyl radical. According to one especially preferred embodiment, this alkyl radical is a non-branched alkyl radical. The chain length of this alkyl radical is not further restricted. For example, this alkyl radical can have 1-20 carbon atoms, thus for example 1-12 carbon atoms, 1-8 carbon atoms, 1-4 carbon atoms or 1 or 2 carbon atoms. The alkyl radical can be, in particular, a methyl radical, an ethyl radical, a propyl radical or a butyl radical. In the radical $R^2$, the index m can assume a whole number in the range of 0-12, preferably in the range of 0-10, even more preferred in the range of 0-8, very especially preferred in the range of 0-6, and in particular in the range of 0-3. For example, the index m can assume the number 2.

According to a second alternative (2) the radical $R^2$ comprises hydrogen. In this case, the radical $R^1$ stands for the radical —$CH_2(CH_2)_mCOOR^3$. In this radical, $R^3$ stands for an alkyl radical. The alkyl radical can involve a branched or non-branched alkyl radical. According to one especially preferred embodiment, this alkyl radical is a non-branched alkyl radical. The chain length of this alkyl radical is not further restricted. For example, this alkyl radical can have 1-20 carbon atoms, thus for example 1-12 carbon atoms, 1-8 carbon atoms, 1-4 carbon atoms, or 1 or 2 carbon atoms. The alkyl radical can be, in particular, a methyl radical, an ethyl radical, a propyl radical or a butyl radical. In the radical $R^2$ the index m can assume a whole number in the range of 0-12, preferably in the range of 0-10, even more preferred in the range of 0-8, very especially preferred in the range of 0-6, and in particular in the range of 0-3. For example, the index m can assume the number 2.

According to a third alternative (3), the radical $R^1$ and the radical $R^2$ form a radical represented by the formula (II)

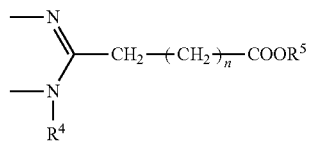

Accordingly, this alternative stands for a heterocyclic ring system with a benzimidazole structure. This can be represented by the following formula (IX)

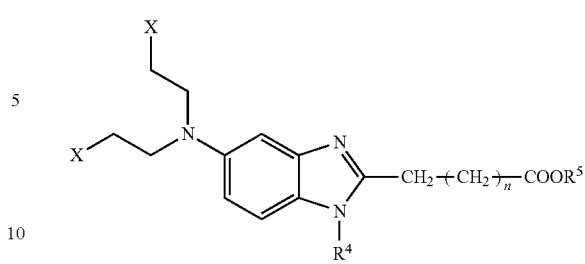

The radical $R^4$ here stands for an alkyl radical. The alkyl radical $R^4$ can involve a branched, but preferably a non-branched alkyl radical. The chain length of this alkyl radical is not further restricted. For example, this alkyl radical can have 1-20 carbon atoms, thus for example 1-12 carbon atoms, 1-8 carbon atoms, 1-4 carbon atoms, or 1 or 2 carbon atoms. The alkyl radical can be, in particular, a methyl radical, an ethyl radical, a propyl radical, or a butyl radical. The radical $R^5$ likewise stands for an alkyl radical. The alkyl radical $R^5$ can likewise involve a branched, but preferably a non-branched alkyl radical. The chain length of this alkyl radical is not further restricted. For example, this alkyl radical can have 1-20 carbon atoms, thus for example 1-12 carbon atoms, 1-8 carbon atoms, 1-4 carbon atoms, or 1 or 2 carbon atoms. The alkyl radical can be, in particular, a methyl radical, an ethyl radical, a propyl radical or a butyl radical. The index n can represent a whole number in the range of 0-10. Preferably, n stands for a whole number in the range of 0-8, more preferably for a whole number in the range of 0-6, even more preferably for a whole number in the range of 0-4, and especially preferably for a whole number in the range of 0-3. For example, the index n can assume the number 2.

According to one preferred embodiment, the compound according to formula (I) comprises 4-[5-[bis(2-chloroethyl)amino]-1-methylbenzimidazole-2-yl]butanoic acid alkyl ester or 4-[bis(2-chloroethyl)amino]benzenebutanoic acid alkyl ester. According to one especially preferred embodiment, the compound according to formula (I) comprises 4-[5-[bis(2-chloroethyl)amino]-1-methylbenzimidazole-2-yl]butanoic acid ethyl ester or 4-[bis(2-chloroethyl)amino]benzenebutanoic acid ethyl ester.

According to the invention, not only the ester described above, but also a salt thereof can be produced. In this salt, preferably at least one of the nitrogen atoms of the compound according to formula (I), in particular the nitrogen atom that is not part of the ring structure, is protonated. The protonated ester is then present in combination with a corresponding anion. This anion preferably comprises a halogenide ion. According to one especially preferred embodiment, the ester is present as a hydrochloride. According to a very especially preferred embodiment, it comprises the hydrochloride of 4-[5-[bis(2-chloroethyl)amino]-1-methylbenzimidazole-2-yl]butanoic acid alkyl ester or 4-[bis(2-chloroethyl)amino]benzenebutanoic acid alkyl ester, as for example 4-[5-[bis(2-chloroethyl)amino]-1-methylbenzimidazole-2-yl]butanoic acid ethyl ester or 4-[bis(2-chloroethyl)amino]benzenebutanoic acid ethyl ester.

As the educt for the production of the compound according to formula (I), a compound represented by the formula (III)

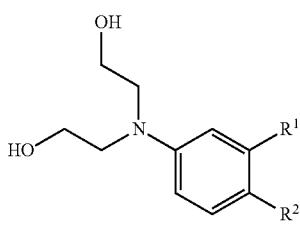

is used. Here, the radicals $R^1$, $R^2$, $R^3$, $R^4$ and $R^5$, as well as the indexes m and n assume the meanings assigned to them above. According to one preferred embodiment, this educt comprises 4-[5-[bis(2-hydroxyethyl)amino]-1-methylbenzimidazole-2-yl]butanoic acid alkyl ester or 4-[bis(2-hydroxyethyl)amino]benzenebutanoic acid alkyl ester, in particular 4-[5-[bis(2-hydroxyethyl)amino]-1-methylbenzimidazole-2-yl]butanoic acid ethyl ester or 4-[bis(2-hydroxyethyl)amino]benzenebutanoic acid ethyl ester.

This educt is brought into reaction with a mixture that contains at least one compound (i) and one compound (ii).

Compound (i) is selected from the group consisting of a compound represented by the formula (IV)

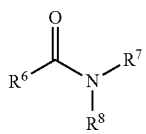

and a compound represented by the formula (V)

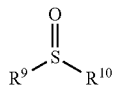

In the compound according to formula (IV), the radical $R^6$ stands for hydrogen or for an alkyl radical. As the alkyl radical, branched, but preferably non-branched alkyl radicals can be used. These alkyl radicals can preferably comprise 1-12 carbon atoms, more preferably 1-10 carbon atoms, even more preferably 1-6 carbon atoms, especially preferred 1-4 carbon atoms, very especially preferred 1-2 carbon atoms, and in particular one carbon atom.

The radicals $R^7$ and $R^8$ stand independently for alkyl radicals. Here, branched, but preferably non-branched alkyl radicals can also be used as the alkyl radical. These alkyl radicals can comprise preferably 1-12 carbon atoms, more preferred 1-10 carbon atoms, even more preferred 1-6 carbon atoms, especially preferred 1-4 carbon atoms, and very especially preferred 1-2 carbon atoms.

Especially preferred compounds according to formula (V) are dimethylformamide (DMF) and dimethylacetamide (DMAc).

The radicals $R^9$ and $R^{10}$ in formula (V) stand independently for alkyl radicals. In turn, branched, but preferably non-branched alkyl radicals can be used as the alkyl radical. These alkyl radicals can preferably comprise 1-12 carbon atoms, more preferred 1-10 carbon atoms, even more preferred 1-6 carbon atoms, especially preferred 1-4 carbon atoms, very especially preferred 1-2 carbon atoms, and in particular one carbon atom. One preferred compound according to formula (V) is dimethyl sulfoxide (DMSO).

The compound (ii) comprises a compound represented by the formula (VI)

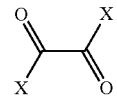

where X stands for a halogen radical, preferably for chlorine. Accordingly, oxalyl chloride is preferred as the compound according to formula (VI).

According to one preferred embodiment of the invention, a 4-[5-[bis(2-chloroethyl)amino]-1-methylbenzimidazole-2-yl]butanoic acid alkyl ester or a salt thereof is produced by the reaction of 4-[5-[bis(2-hydroxyethyl)amino]-1-methylbenzimidazole-2-yl]butanoic acid alkyl ester with oxalyl chloride and dimethylformamide. According to one especially preferred embodiment, a 4-[5-[bis(2-chloroethyl)amino]-1-methylbenzimidazole-2-yl]butanoic acid ethyl ester or a hydrochloride thereof is produced by bringing 4-[5-[bis(2-hydroxyethyl)amino]-1-methylbenzimidazole-2-yl]butanoic acid ethyl ester into reaction with oxalyl chloride and dimethylformamide.

The compound (ii) represented by the formula (VI) is used at least equimolar, but preferably in molar excess, relative to the compound according to formula (III). According to one especially preferred embodiment, the molar ratio of the compound according to formula (VI) to the compound according to formula (III) is at least 1.3 and even more preferred at least 1.5.

In one preferred embodiment of the invention, initially the compounds (i) (i.e., the compounds according to the formulas (IV) and/or (V)) and (ii) (i.e., the compound according to formula (VI)) are combined with each other and then brought into contact with the compound according to formula (III). For this purpose, the compounds (i) and (ii) as well as the compound according to formula (III) are present both individually and also combined preferably in a suitable solvent. As the solvent, for example, halogenated hydrocarbons, such as dichloromethane or chloroform, or other aprotic solvents, such as tetrahydrofuran or dioxane, can be used.

Preferably, for the method according to the invention, the compound according to formula (VI) dissolved in a suitable solvent is provided in a reaction vessel and optionally cooled, wherein temperatures in the range of 0-10° C., thus for example temperatures in the range of 1-5° C. or in the range of 1-3° C., have proven to be especially advantageous.

The compound according to formula (IV) or formula (V) is also preferably dissolved in a suitable solvent and then optionally cooled. Here, temperatures in the range of 0-10° C., thus for example temperatures in the range of 1-5° C. or in the range of 1-3° C., have also proven especially advantageous.

According to one possible embodiment of the invention, in a next step, the compound according to formula (VI) and the compound according to formula (IV) or (V) are combined. This can be carried out, for example, in that the solution that contains the compound according to formula (VI) is added, for example dropwise, to the solution that contains the compound according to formula (IV) or (V). Obviously, however, the solution that contains the compound according to formula (IV) or (V) can also be added, for example dropwise, to the solution that contains the compound according to formula (VI). In this step, accordingly a solution is preferably obtained that comprises the compounds (i) and (ii).

This solution is now mixed preferably with a solution that contains the compound according to formula (III). For this purpose, for example, the solution that contains the compound according to formula (III) can be added dropwise to the solution that contains the compounds (i) and (ii).

The reaction of the compounds contained in the resulting reaction mixture can then be controlled by a method familiar to one skilled in the art. For example, the reaction mixture can be stirred with recycling.

The stirring of the reaction mixture with recycling can be carried out, for example, for a time period of at least one hour, preferably for a time period of at least two hours, even more preferred for a time period of at least four hours, and especially preferred for a time period of at least six hours. According to one preferred embodiment, the stirring of the reaction mixture with recycling is carried out for a time period of 1-24 hours, more preferred for a time period of 2-20 hours, even more preferred for a time period of 4-16 hours, and especially preferred for a time period of 6-12 hours.

The reaction can optionally be carried out in an inert-gas atmosphere, thus for example in a nitrogen atmosphere or in a noble-gas atmosphere.

After the reaction, the reaction product is present, according to the pH value of the reaction mixture, as a free base or as a salt. For example, the reaction product according to formula (I) comprises bendamustine ethyl ester, so this is present, at pH values $\geq 7.5$, as a free base, at lower pH values, as a salt, for example as a hydrochloride. In this respect, it is possible to obtain the reaction product according to formula (I) as a free base or else as a salt by setting the pH value to a suitable value.

After the reaction, the reaction product represented by the formula (I) can be isolated from the reaction mixture according to a first embodiment. Alternatively, according to a second embodiment, however, the reaction mixture can also be used directly for carrying out an ester hydrolysis, in order to produce the product according to formula (VII).

If isolation of the reaction product according to formula (I) from the reaction mixture is desired, then this can be carried out in a conventional way. For example, the reaction mixture can be mixed with water, in order to generate an organic and an aqueous phase. While the organic phase contains the reaction product according to formula (I), the aqueous phase is used to remove water-soluble components, as for example salts, from the organic phase.

In a next step, if desired or necessary, the pH value can be set, in order to convert the reaction product according to formula (I) into the free base or else a corresponding salt. If the reaction product is present in the reaction mixture, for example as a salt, then by adding a base the pH value of the reaction mixture can be increased, in order to convert the salt into the free base. This can be carried out, for example, by the addition of basic solutions, such as potassium carbonate, to the reaction mixture mixed with water.

Then, the mixture made from the reaction mixture and water is preferably mixed intensively, in order to allow a transfer of water-soluble components from the organic phase into the aqueous phase. The organic phase is then preferably removed from the mixture and neutralized, while the aqueous phase is mixed and extracted with an organic solvent, thus for example with the solvent or one of the solvents that has been used for dissolving the compounds according to formula (III) or the compounds (i) and (ii) before the reaction. The organic phase or the combined organic phase can then be dried, for example, in a vacuum until reaching weight constancy, in order to obtain the reaction product according to formula (I).

The reaction product according to formula (I) is typically used as an intermediate for the production of a compound represented by the formula (VII)

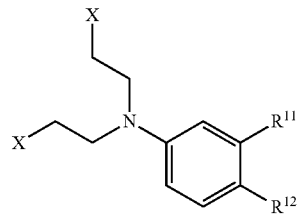

or a salt thereof.

In formula (VII) X stands, in turn, for a halogen atom, preferably for a chlorine atom or a bromine atom and especially preferred for a chlorine atom.

The radicals $R^{11}$ and $R^{12}$ can assume different meanings.

According to a first alternative (1), the radical $R^{11}$ comprises hydrogen. In this case, the radical $R^{12}$ stands for the radical $-CH_2(CH_2)_m COOH$. In the radical $R^{12}$ the index m can assume a whole number in the range of 0-12, preferably in the range of 0-10, even more preferred in the range of 0-8, very especially preferred in the range of 0-6, and in particular in the range of 0-3. For example, the index m can assume the number 2.

According to a second alternative (2), the radical $R^{12}$ comprises hydrogen. In this case, the radical $R^{11}$ stands for the radical $-CH_2(CH_2)_m COOH$. In the radical $R^{12}$ the index m can assume a whole number in the range of 0-12, preferably in the range of 0-10, even more preferred in the range of 0-8, very especially preferred in the range of 0-6, and in particular in the range of 0-3. For example, the index m can assume the number 2.

According to a third alternative (3), the radical $R^{11}$ and the radical $R^{12}$ form a radical represented by the formula (VIII)

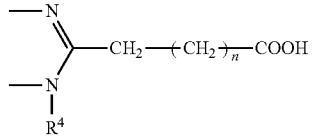

Accordingly, this alternative stands for a heterocyclic ring system with a benzimidazole structure. This can be represented by the following formula (X)

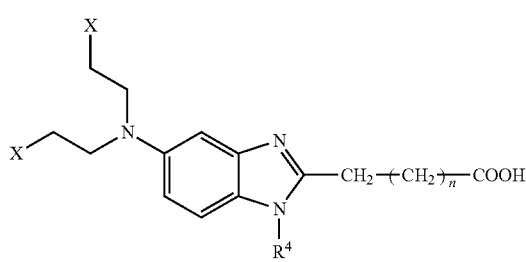

Here, the radical $R^4$ stands for an alkyl radical. The alkyl radical $R^4$ can involve a branched, but preferably a non-branched alkyl radical. The chain length of this alkyl radical is not further restricted. For example, this alkyl radical can have 1-20 carbon atoms, thus for example 1-12 carbon atoms, carbon atoms, 1-4 carbon atoms, or 1 or 2 carbon atoms. The alkyl radical can be, in particular, a methyl radical, an ethyl radical, a propyl radical, or a butyl radical. The index n can represent a whole number in the range of 0-10. Preferably, n stands for a whole number in the range of 0-8, more preferably for a whole number in the range of 0-6, even more preferred for a whole number in the range of 0-4, and especially preferred for a whole number in the range of 0-3. For example, the index n can assume the number 2.

According to one preferred embodiment, the compound according to formula (I) comprises 4-[5-[bis(2-chloroethyl)amino]-1-methylbenzimidazole-2-yl]butanoic acid or 4-[bis(2-chloroethyl)amino]benzenebutanoic acid.

According to the invention, not only the acid described above, but also a salt thereof can be produced. In this salt, preferably at least one of the nitrogen atoms of the compound according to formula (I), in particular the nitrogen atom that is not part of the ring structure, is protonated. The protonated ester is then present in combination with a corresponding anion. This anion preferably comprises a halogenide ion. According to one especially preferred embodiment, the ester is present as a hydrochloride. According to one very especially preferred embodiment, it comprises a hydrochloride of 4-[5-[bis(2-chloroethyl)amino]-1-methylbenzimidazole-2-yl]butanoic acid or 4-[bis(2-chloroethyl)amino]benzenebutanoic acid.

For the production of the compound according to formula (VII), initially the method described above for the production of the compound according to formula (I) is carried out and the resulting reaction product undergoes an ester hydrolysis. For this purpose, the resulting reaction product can be either, as described above, initially isolated and then hydrolyzed or else converted directly (i.e., without prior isolation) into acid.

According to one especially preferred embodiment, in the scope of the invention, 4-[5-[bis(2-chloroethyl)amino]-1-methylbenzimidazole-2-yl]butanoic acid or a salt thereof is produced in that, in a first step a 4-[5-[bis(2-hydroxyethyl)amino]-1-methylbenzimidazole-2-yl]butanoic acid alkyl ester or a salt thereof is reacted with oxalyl chloride and dimethylformamide under formation of a 4-[5-[bis(2-chloroethyl)amino]-1-methylbenzimidazole-2-yl]butanoic acid alkyl ester or a salt thereof, and in a second step the resulting 4-[5-[bis(2-chloroethyl)amino]-1-methylbenzimidazole-2-yl]butanoic acid alkyl ester or a salt thereof is hydrolyzed.

For the ester hydrolysis, the reaction product according to formula (I) is preferably mixed with an acid. Here, preferably an inorganic acid, in particular hydrochloric acid, is used as the acid. The acid is typically used as a concentrated acid, for example as a concentrated hydrochloric acid (32%). By the pH value decrease to be traced back to the addition of acid, the reaction product according to formula (I), which is instable for stronger basic pH values, is stabilized.

The reaction product according to formula (I) can be mixed with the acid, in that the acid is combined with the isolated reaction product according to formula (I), with a solution of the isolated reaction product according to formula (I) in a suitable solvent, or with the reaction mixture that is described above and contains the isolated reaction product according to formula (I).

Then the resulting mixture is stirred preferably at a temperature in the range of 10-80° C., more preferred at a temperature in the range of 15-70° C., and even more preferred at a temperature in the range of 20-60° C.

The reaction period preferably equals 30 minutes to six hours, more preferred one hour to four hours, and even more preferred one hour to three hours.

After the reaction, organic components possibly contained in the mixture, as for example solvents or solvent radicals, can be removed. This can be performed preferably by distillation of these organic components.

In another optional step the mixture, which contains, in addition to the acid, the now hydrolyzed ester according to formula (VII), is mixed with active carbon and stirred. The active carbon can be used to bind, by absorption, possible contaminants contained in the mixture. The active carbon can then be separated from the remainder of the mixture, e.g. through filtration.

The acid contained in the mixture is then removed in a conventional way from the hydrolyzed ester according to formula (VII). For this purpose, the acid is preferably separated by distillation from the hydrolyzed ester according to formula (VII). The compound according to formula (VII) remains as a residue, which can be present, for example, as a solid or as an oily fluid.

If necessary, the residue can be further purified. If the residue is present, for example as an oily fluid, then initially a precipitate of the compound according to formula (VII) can be generated with a suitable solution. As the precipitate solution, in particular, mixtures can be used that contain water and furthermore a ketone or an alcohol. Here, acetone has proven itself as a suitable ketone, ethanol as a suitable alcohol. After the precipitation, the obtained residue can be separated from the precipitate solution.

If necessary, the remaining residue can be subsequently washed with a suitable washing solution and then dried. As the washing solution, preferably water and ethyl acetate can be used.

The invention will be described by the following examples, which however are not to be understood as limiting.

Example 1a

Production of Bendamustine Ethyl Ester 26.7 g oxalyl chloride (1.6 equivalents) was dissolved in 279 ml dichloromethane and cooled to 1° C. At 1° C. a mixture of 17 ml dimethylformamide (DMF) and 50 ml dry dichloromethane was added slowly. A solution of 23 g ethyl-4-(5-(bis-(2-hydroxyethyl)-amino)-1-methyl-1H-benzo[d]imidazol-2-yl)butanoate in 115 ml dichloromethane was added to the resulting reaction mixture. The reaction mixture was stirred for 8 hr with recycling (45° C. jacket temperature), cooled and then mixed with 50 ml ultra-pure water. Through the addition of 25% $K_2CO_3$ solution, the pH value was adjusted to pH 8-9.5. After intensive thorough mixing, the organic phase was separated and the aqueous phase was extracted with additional 83 ml dichloromethane. The combined organic phases were dried in a vacuum until reaching weight constancy.

This experiment was carried out six times. The following yields of bendamustine ethyl ester were obtained:

| Exp. 1a-1 | Exp. 1a-2 | Exp. 1a-3 | Exp. 1a-4 | Exp. 1a-5 | Exp. 1a-6 | Average Yield | Maximum Deviation from Average Yield |
|---|---|---|---|---|---|---|---|
| 93.2% | 92.7% | 92.5% | 90.4% | 93.4% | 93.0% | 93.0% | +0.4%/−2.6% |

Example 1b

Production of Bendamustine

The bendamustine ethyl ester raw product obtained in Example 1a was dissolved in 210 ml 32% HCl and stirred for 2 hr at 40° C. jacket temperature. The solution was cooled to room temperature, mixed with 8 g active carbon, stirred for 30 min and filtered through a sterile filter. The hydrochloric acid was separated by distillation and the residue was mixed with 400 ml water/acetone. The precipitate was filtered out, washed with water and ethyl acetate and dried.

This experiment was carried out twice. The following yields of bendamustine were obtained, each with respect to the method starting from ethyl-4-(5-(bis-(2-hydroxyethyl)-amino)-1-methyl-1H-benzo[d]imidazol-2-yl)butanoate:

| Exp. 1b-1 | Exp. 1b-2 | Average Yield | Maximum Deviation from Average Yield |
|---|---|---|---|
| 82.0% | 77.6% | 79.8% | +2.2%/−2.2% |

Comparison Example 2a

Production of Bendamustine Ethyl Ester

An alternative method for the production of bendamustine alkyl ester likewise starts from an ethyl-4-(5-(bis-(2-hydroxyethyl)amino)-1-methyl-1H-benzo[d]imidazol-2-yl) alkyl ester as educt. Here, the outgoing trend of the hydroxyl groups in this educt is increased by the addition of an activation group (for example a p-tosyl group, a mesyl group or a triflate group). The exchange of this activation group by a halogenide is then possible under mild conditions, for example by treatment with lithium chloride in dimethylformamide or ethanol.

In a corresponding experiment, 42.2 g ethyl-4-(5-(bis-(2-hydroxyethyl)amino)-1-methyl-1H-benzo[d]imidazol-2-yl) butanoate) were dissolved in 500 ml dry dichloromethane and mixed with 41.6 ml triethylamine (TEA). This solution was slowly mixed with 52.2 g methane sulfonic acid anhydride in 150 ml dry dichloromethane and stirred for 3 hr at 25° C. The reaction solution was freed from solvents at 30° C. in a vacuum. The obtained residue was dissolved in 400 ml dry ethanol, mixed with 30.5 g lithium chloride and stirred for 18 hr at 70° C. Then, ethanol was separated by distillation at 40° C. and the residue imbibed in 400 ml dichloromethane (DCM) and mixed with 16.6 ml triethylamine (TEA). After the addition of 200 ml water, the pH value was adjusted with concentrated $K_2CO_3$ solution to between 7.5 to 9. The resulting phases are separated, the aqueous phase extracted with additional 250 ml DCM, the purified organic phases washed with 100 ml half-concentrated sodium chloride solution, dried over $MgSO_4$, and freed from the solvent in a vacuum.

This experiment was carried out four times. The following yields of bendamustine ethyl ester were obtained:

| Exp. 2a-1 | Exp. 2a-2 | Exp. 2a-3 | Exp. 2a-4 | Average Yield | Maximum Deviation from Average Yield |
|---|---|---|---|---|---|
| 82.9% | 85.2% | 81.9% | 80.1% | 82.5% | +2.7%/−2.4% |

Comparison Example 2b

Production of Bendamustine

The bendamustine ethyl ester raw product obtained in Comparison Example 2a was dissolved in 210 ml 32% HCl and stirred for 2 hr at 40° C. jacket temperature. The solution was cooled to room temperature, mixed with 8 g active carbon, stirred for 30 min, and filtered through a sterile filter. The hydrochloric acid was separated by distillation and the residue was mixed with 400 ml water/acetone. The precipitate was filtered out, washed with water and ethyl acetate, and dried.

This experiment was carried out twice. The following yields of bendamustine were obtained, each with respect to the method starting from ethyl-4-(5-(bis-(2-hydroxyethyl)-amino)-1-methyl-1H-benzo[d]imidazol-2-yl)butanoate:

| Exp. 2b-1 | Exp. 2b-2 | Average Yield | Maximum Deviation from Average Yield |
|---|---|---|---|
| 69.8% | 71.3% | 70.6% | +0.5%/−0.8% |

Comparison Example 3a

Production of Bendamustine Ethyl Ester

Bendamustine ethyl ester was produced by following the specific example of DD 159877. Then, 18.3 mol thionyl chloride (2.175 kg) was used to substitute 22.3 mol hydroxyl groups (in 4.305 kg 4-[5-[bis(2-Hydroxyethyl)amino]-1-methylbenzimidazole-2-yl]butanoic acid ethyl ester). This resulted in only an incomplete conversion, however, where only approximately 47 area % of the desired product was obtained in the reaction mixture.

For this reason, the quantity of thionyl chloride was increased in further experiments. A tripling of the quantity of thionyl chloride in the ratio to 4-[5-[bis(2-Hydroxyethyl) amino]-1-methylbenzimidazole-2-yl]butanoic acid ethyl ester (from 0.82 equivalents according to DD 159877 to 2.46 equivalent) led to 87 area % of the desired product and represented the optimum of the studied variations.

The following yields of bendamustine ethyl ester were obtained:

| Exp. 3a-1 | Exp. 3a-2 | Average Yield | Maximum Deviation from Average Yield |
|---|---|---|---|
| 75.0% | 59.0% | 67.0% | +8.0%/−8.0% |

The material obtained according to the preceding procedure did not satisfy the specification requirements of the ICH Guidelines despite recrystallization performed two times.

These experiments show that the method according to the invention surprisingly delivers a significantly increased, reproducible yield, compared with the method known from the prior art.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for production of a compound represented by formula (I)

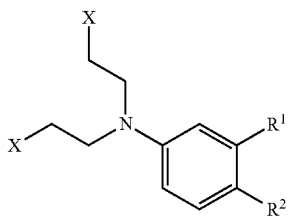

or a salt thereof, where X stands for a halogen radical, $R^1$ and $R^2$ are selected so that (1) $R^1$ is H and $R^2$ is $CH_2(CH_2)_mCOOR^3$, (2) $R^1$ is $CH_2(CH_2)_mCOOR^3$ and $R^2$ is H, or (3) $R^1$ and $R^2$ together stand for a radical represented by formula (II)

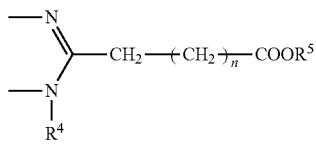

where each of $R^3$, $R^4$ and $R^5$ stands independently for an alkyl radical, and where each of m and n represents independently a number in a range of 0-12, the method comprising reacting a compound represented by formula (III)

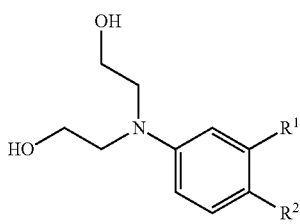

with a mixture containing a compound (i) selected from the group consisting of a compound represented by formula (IV)

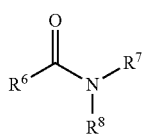

where $R^6$ stands for H or an alkyl radical, and each of $R^7$ and $R^8$ stands independently for an alkyl radical, and of a compound represented by formula (V)

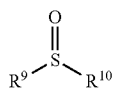

where each of $R^9$ and $R^{10}$ stands independently for an alkyl radical, and this mixture also contains a compound (ii) represented by formula (VI)

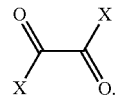

2. The method according to claim 1, wherein X represents a chloride.

3. The method according to claim 1, wherein $R^1$ and $R^2$ together stand for a radical represented by formula (II).

4. The method according to claim 3, wherein n is a whole number in range of 1-3.

5. The method according to claim 4, wherein $R^4$ stands for an alkyl radical selected from the group consisting of a methyl radical, an ethyl radical, and a propyl radical.

6. The method according to claim 5, wherein $R^4$ stands for a methyl radical.

7. The method according to claim 1, wherein $R^5$ stands for an alkyl radical selected from the group consisting of a methyl radical, an ethyl radical, a propyl radical, and a butyl radical.

8. The method according to claim 1, wherein $R^1$ is H and $R^2$ is $CH_2(CH_2)_mCOOR^3$.

9. The method according to claim 8, wherein m is a whole number in a range of 1-3.

10. The method according to claim 9, wherein m is equal to 2.

11. The method according to claim 1, wherein the compound represented by formula (IV) is a dialkylformamide.

12. The method according to claim 11, wherein the dialkylformamide is dimethylformamide.

13. The method according to claim 1, wherein the compound represented by formula (IV) is dimethylacetamide.

14. The method according to claim 1, wherein the compound represented by formula (V) is dimethyl sulfoxide.

15. The method according to claim 1, wherein the compound represented by formula (VI) is oxalyl chloride.

16. The method according to claim 1, wherein a molar ratio of the compound according to formula (VI) to the compound according to formula (III) equals at least 1.3.

17. The method according to claim 1, wherein the reaction is carried out in a chlorinated solvent or an aprotic solvent.

18. A method for production of a compound represented by formula (VII)

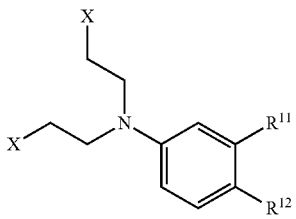

or a salt thereof, where X stands for a halogen radical, $R^{11}$ and $R^{12}$ are selected so that (1) $R^{11}$ is H and $R^{12}$ is $CH_2(CH_2)_mCOOH$, (2) $R^{11}$ is $CH_2(CH_2)_mCOOH$ and $R^{12}$ is H, or (3) $R^{11}$ and $R^{12}$ together stand for a radical represented by the formula (VIII)

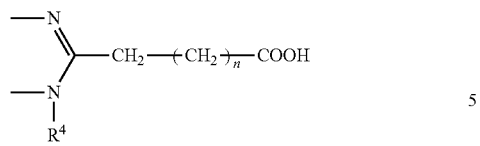
where R⁴ stands for an alkyl radical and where each of m and n represents independently a number in the range of 0-12,
wherein the method is carried out according to claim 1, and a resulting ester compound represented by formula (I) undergoes ester hydrolysis.
\* \* \* \* \*